United States Patent [19]

Bavitz et al.

[11] Patent Number: 4,910,022
[45] Date of Patent: Mar. 20, 1990

[54] PHTHALAZINEACETIC ACID COMPOSITION AND TABLET

[75] Inventors: Joseph F. Bavitz, Huntington Valley; Ashok V. Katdare, Norristown, both of Pa.

[73] Assignee: Merck & Co., Inc., Rahway, N.J.

[21] Appl. No.: 270,883

[22] Filed: Nov. 15, 1988

Related U.S. Application Data

[63] Continuation-in-part of Ser. No. 115,810, Nov. 2, 1987, abandoned.

[51] Int. Cl.⁴ ................................................ A61K 9/20
[52] U.S. Cl. .................................... 424/465; 424/474; 424/478; 424/479; 424/480; 514/248
[58] Field of Search ......................... 514/248; 544/237; 424/478, 479, 480, 474, 464, 465

[56] References Cited

U.S. PATENT DOCUMENTS

| | | | |
|---|---|---|---|
| 4,251,528 | 2/1981 | Brittain et al. | 424/250 |
| 4,393,062 | 7/1983 | Brittain et al. | 424/250 |
| 4,439,453 | 3/1984 | Vogel | 424/324 |
| 4,444,769 | 4/1984 | Blume et al. | 424/246 |
| 4,463,172 | 7/1984 | Horii et al. | 540/227 |
| 4,555,399 | 11/1985 | Hsiao | 424/465 |
| 4,609,675 | 9/1986 | Franz | 514/568 |
| 4,616,008 | 10/1986 | Hirai et al. | 514/200 |

*Primary Examiner*—Thurman K. Page
*Attorney, Agent, or Firm*—Alice O. Robertson; Joseph F. DiPrima

[57] ABSTRACT

A tablet composition for a phthalazineacetic acid compound to be employed in treating clinical effects associated with diabetes is described. The composition permits formation of tablets having a relatively high dose of drug in a relatively small size useful for gaining patient compliance. The preferred phthalazineacetic acid compound is 3-((4-bromo-2-fluorophenyl)methyl)-3,4-dihydro-4-oxo-1-phthalazineacetic acid.

5 Claims, No Drawings

PHTHALAZINEACETIC ACID COMPOSITION AND TABLET

This application is a continuation-in-part of application Ser. No. 115,810, filed on Nov. 2, 1987 and now abandoned.

This invention is directed to a pharmaceutical tablet and a composition therefor.

BACKGROUND OF THE INVENTION

The enzyme aldose reductase acts to catalytically convert aldoses such as glucose and galactose to their corresponding alditols. The alditols, thus formed, tend to accumulate in the cell giving rise to osmotic pressures which may impair the function of the cells. The enzyme acts primarily when the concentration of an aldose is high such as in diabetics, thus giving rise to clinical conditions in diabetes such as retinopathy, neuropathy, nephropathy and the like. Certain phthalazin-4-yl-acetic acid compounds have been found to be useful in the reduction or prevention of the clinical effects associated with diabetes. These compounds are described in U.S. Pat. Nos. 4,251,528 and 4,393,062. A particularly useful compound is 2-(2-fluoro-4-bromobenzyl)-1,2-dihydro-1-oxophthalazin-4-yl-acetic acid which may be identified also by the Chemical Abstracts system of nomenclature as 3-((4-bromo-2-fluorophenyl)methyl)-3,4-dihydro-4-oxo-1-phthalazineacetic acid and represented by Formula I.

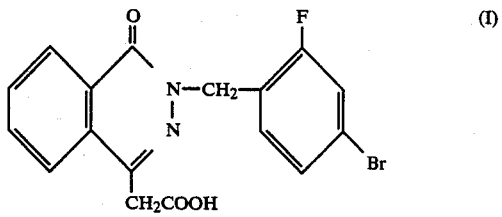

A pharmaceutical tablet of the compound of Formula I has been disclosed in the aforecited U.S. Pat. No. 4,393,062. It has been found however that when tablets are prepared wit the formulation as described in said patent or are prepared using a number of the conventional tablet formulating ingredients, the amount and/or kind of tablet ingredients are such as to necessitate for the required dose of drug, either a large tablet or a tablet containing less than the quantity of drug desired for said dose, thereby requiring multiple dosing. It is desirable to have a small tablet which would be easy to swallow but containing the entire required dosage enabling once a day administration thereby encouraging patient compliance, and which tablet would also have the appropriate physicochemical properties for efficient and effective utilization of the drug such as rapid disintegration and dissolution.

STATEMENT OF INVENTION

The present invention is directed towards an improved pharmaceutical tablet composition comprising the compound of Formula I, disclosed and claimed in the aforecited U.S. Pat. Nos. 4,251,528 and 4,393,062, and hereinafter referred to as the phthalazineacetic acid compound and to tablets prepared therefrom. The tablets according to the present invention have superior physico-chemical properties and further may be prepared in a size easy to swallow while still containing the entire required dosage for single administration.

DESCRIPTION OF THE INVENTION

The present invention is directed to a new composition which comprises a blend of the phthalazineacetic acid compound with a minimal amount of selected tablet ingredients and processing aids and to the tablets formed therewith.

The invention is particularly directed to compositions containing 3-((4-bromo-2-fluorophenyl)methyl)-3,4-dihydro-4-oxo-1-phthalazineacetic acid as the phthalazineacetic acid compound. In the therapeutic applications of this drug, both high and low dose levels may be used depending on patient size and other factors, and 300 mg and 600 mg doses have been found to be most useful. Hence, the invention is directed to tablet compositions which would be adaptable to preparing tablets which supply either low or high dose amounts in a readily swallowable small single tablet which tablet would also have superior physico-chemical properties.

The tablet composition of the present invention contains by weight from about 83 to 88 percent of the phthalazineacetic acid compound, about 8 to 20 percent of a diluent, about 1 to 4 percent of a disintegrant, about 1 to 4 percent of a binder and about 0.5 to 2 percent of a lubricant.

The ingredients of the tablet composition are selected from a limited group of excipients. The diluent contemplated is microcrystalline cellulose. The disintegrant may be one of several modified starches or modified cellulose polymers, preferably croscarmellose sodium, or a mixture thereof. The binder may be gelatin, a modified starch, preferably pregelatinized starch, or a mixture thereof. Suitable lubricants include magnesium or calcium stearate, preferably magnesium stearate. It is desirable to include a small amount (about 0.25 to 0.35 percent) of wetting agent such as sodium lauryl sulfate or docusate sodium (dioctyl sulfosuccinate sodium). Although a mixture of excipients may be employed for each functional class, generally it is preferred that a single excipient be selected for each function.

Microcrystalline cellulose is substantially the only diluent found useful for obtaining a tablet of the desired properties in the desired dosage and size with phthalazineacetic acid as drug. Microcrystalline cellulose is a non-fibrous form of cellulose in which the cell wall of plant fibers has been broken into fragments ranging in size from a few hundred microns to a few tenths of a micron in length. It is chemically identical to native cellulose and has the same X-ray diffraction pattern. It is available commercially under trade name "Avicel" from FMC Corporation. It is to be distinguished from cellulose derivatives such as soluble sodium carboxymethylcellulose which is commonly used as a binder but is not suitable in the amounts contemplated. It is also to be distinguished from croscarmellose sodium, an insoluble cross-linked carboxymethylcellulose which is used in minor amounts as disintegrant.

The preferred tablet composition of the present invention contains by weight from about 83 to 88 percent 3-((4-bromo-2-fluorophenyl)methyl)3,4-dihydro-4-oxo-1-phthalazineacetic acid, about 8 to 20 percent microcrystalline cellulose, about 1 to 4 percent pregelatinized starch, about 1 to 4 percent croscarmellose sodium, and about 0.5 to 1.5 percent magnesium stearate, and about 0.25 to 0.35 percent sodium lauryl sulfate.

Representative of the most preferred tablets and supplying 300 mg and 600 mg of the drug are tablets of the following compositions.

TABLE I

| Component | TABLET A | TABLET B |
|---|---|---|
| | mg/tablet | |
| Compound Formula I | 300.0 | 600.0 |
| Pregelatinized starch (NF 1551) | 10.0 | 20.0 |
| Sodium lauryl sulfate NF | 1.0 | 2.0 |
| Microcrystalline cellulose NF | 31.0 | 62.0 |
| Croscarmellose Sodium NF | 5.0 | 10.0 |
| Magnesium stearate NF | 3.0 | 6.0 |

The tablets formed of the foregoing compositions are consistent in quality, hold the required relatively high doses of drug in a size suitable for gaining patient compliance and generally have excellent physico-chemical qualities. Thus, for example, the foregoing 300 mg (drug weight) tablet has been found to have the following properties:

| | |
|---|---|
| Tablet weight | 350 milligrams |
| Tablet hardness[1] (10)* | 12–14 kilopounds (average) |
| Disintegration time[2] (6)* | 1 to 2 minutes (range) |
| Friability[3] (28)* | 0.16 percent loss |
| Dissolution rate[4] (6)* | |
| 10 minutes | 77% (average) |
| 20 minutes | 88% (average) |
| 30 minutes | 90% (average) |

*Number in parenthesis indicates number of tablets used
[1]Schleuniger hardness tester
[2]USP disintegration apparatus II
[3]Roche friability tester, 16 minutes
[4]USP dissolution method, apparatus II Tablets having higher and lower doses of the drug have similar desirable properties when produced in the above-described composition range. Thus, representative 600 mg tablets have been prepared having the following properties:

| | |
|---|---|
| Tablet weight | 700 milligrams |
| Tablet hardness (10) | 11–13 kilopounds |
| Disintegration time (6) | 1 to 2 minutes |
| Friability (14) | 0.25 percent loss |
| Dissolution rate (6) | |
| 15 minutes | 77% |
| 30 minutes | 92% |
| 45 minutes | 96% |
| 60 minutes | 99% |

From the foregoing it can be seen that the tablet compositions of high drug content can be used to prepare drugs which have outstanding properties. Thus, the tablets show hardness well above the 6 kiloponds which is considered the lower limit for these sizes. In fact, tablets having hardness up to 19–20 kiloponds have been prepared employing the same ratio of ingredients but by varying the amounts of granulating fluid during manufacture. Friability values of 1 percent or less for 100 revolutions and satisfactory dissolution rates are achieved well within the standard of the USP test method.

The tablets may be prepared by 1) mixing the phthalazineacetic acid compound, pregelatinized starch and microcrystalline cellulose in a planetary mixer or a high speed mixer for time sufficient to insure thorough mixing; (2) dissolving sodium lauryl sulfate in a suitable amount of water at room temperature; (3) adding the aqueous mixture of Step (2) to the powder mixture of Step (1) to granulate the powder mixture; (4) passing the granulated mixture through a screen having an opening of 1.7 to 2.4 mm; (5) drying the sized granulated mixture at about 40 60° C., preferably 50° C. for time sufficient to effect drying; (6) passing the dried granulated mixture through a screen having an opening of 0.55 to 0.65 mm; (7) mixing the dry-sized granulation with croscarmellose sodium; (8) adding magnesium stearate which has previously been bolted through a No. 60 screen (0.25 mm opening); (9) blending the resulting mix for time sufficient to obtain the desired lubricated granular tablet formulation, usually about 2 to 5 minutes. Thereafter, the lubricated granular formulation is compressed using a conventional tablet press to form tablets which are then preferably coated. Substances which may be used for coating include hydroxypropylmethylcellulose, hydroxypropylcellulose, titanium oxide, talc and colorants.

The following examples illustrate the invention but are not to be construed as limiting.

EXAMPLE I 900.0 grams of 3-((4-bromo-2-fluorophenyl)methyl)-3,4-dihydro-4-oxo-1-phthalazineacetic acid (previously milled in an Alpine Mill), 33.0 grams of pregelatinized starch NF 1551, and 93.0 grams microcrystalline cellulose NF (Avicel PH 101) were mixed together in a planetary mixer at about 40–45 rpm for 5 minutes. The resulting mixture was passed through a No. 30 sieve (0.59 mm sieve opening). The screened material was mixed for 5 additional minutes.

Three grams of sodium lauryl sulfate was dissolved in 255 milliliters of water and the resulting solution was added to the above powdery mixture over a period of three minutes at 45 to 45 rpm, then for an additional 2 minutes at 60 to 70 rpm. The resulting granulate was passed through a No. 10 screen 2.00 mm sieve opening). The screened granulate was then dried at 50° C. in a fluid bed dryer for approximately 15 minutes. The dried material was sized by passing through sieve No. 20 (0.84 mm sieve opening). 15.0 grams of croscarmellose sodium NF was added, and the resulting mixture blended for 3 minutes in a V-shaped blender.

9.0 grams of magnesium stearate NF was bolted through a No. 60 sieve and to it was added the dry-sized granulation and the resulting mixture blended for 2 minutes to obtain the desired lubricated granular tablet composition.

The composition was fed into a standard single punch tablet press to obtain 3000 tear drop shaped tablets of 300 mg potency, of about 0.282×0.456 cm in size, and having an average weight of about 350 mgs.

EXAMPLE II 1.8 kilograms of 3-((4-bromo-2-fluorophenyl)methyl)-3,4-dihydro-4-oxo-1-phthalazineacetic acid, (previously milled in an Alpine Mill), 66 grams of pregelatinized starch NF 1551, and 186 grams microcrystalline cellulose NF (Avicel PH 101) were mixed together in a planetary mixer at about 40–45 rpm for 5 minutes. The resulting mixture was passed through a No. 30 sieve (0.59 mm sieve opening). The screened material was mixed for 5 additional minutes.

Six grams of sodium lauryl sulfate was dissolved in 510 milliliters of distilled water and the resulting solution was added to the above powdery mixture over a period of three minutes at 45 to 50 rpm, then for two more minutes at 60 to 70 rpm. The resulting granulate was passed through a No. 10 screen (2.00 mm sieve opening). The screened granulate was then dried at 50° C. in a electrical dryer for sixteen hours. The dried material was sized by passing through sieve No. 20 (0.84 mm sieve opening). 30.0 grams of croscarmellose sodium NF was added, and the resulting mixture blended for 5 minutes in a V-shaped blender.

18.0 grams of magnesium stearate NF was bolted through a No. 60 sieve and to it was added the dry-sized granulation and the resulting mixture blended for 3 minutes to obtain the desired lubricated granular tablet composition.

The composition was delivered to a standard single punch tablet press to obtain 3000 elliptical tablets of 600 mg potency of about 0.81×1.47 cm with a thickness of about 5.5 to 5.6 mm and an average weight of about 700 milligrams.

What is claimed is:

1. A tablet composition containing by weight a blend of about 83 to 88 percent of 3-((4-bromo-2-fluorophenyl)methyl)-3,4-dihydro-4-oxo-1-phthalazineacetic acid, about 8 to 20 percent of microcrystalline cellulose as diluent, about 1 to 4 percent of a binder selected from gelatin, modified starch or pregelatinized starch or a combination thereof, about 1 to 4 percent disintegrant selected from modified starch, modified cellulose polymer or croscarmellose sodium or a combination thereof, about 0.5 to 2 percent lubricant selected from magnesium stearate or calcium stearate and 0.25 to 0.35 percent of a wetting agent selected from sodium lauryl sulfate or docusate sodium (dioctyl sulfosuccinate sodium).

2. A composition according to claim 1 in which the binder is modified starch, the disintegrant is croscarmellose sodium, the lubricant is magnesium stearate and the wetting agent is sodium lauryl sulfate.

3. A tablet prepared from the composition of claim 1.

4. A tablet according to claim 3 which is film coated.

5. A tablet prepared from the composition of claim 2.

* * * * *